(12) United States Patent
Sherman et al.

(10) Patent No.: US 6,332,985 B1
(45) Date of Patent: *Dec. 25, 2001

(54) PROCESS FOR REMOVING TOXINS FROM BODILY FLUIDS USING ZIRCONIUM OR TITANIUM MICROPOROUS COMPOSITIONS

(75) Inventors: John D. Sherman, Amherst, MA (US); David S. Bem, Arlington Heights; Gregory J. Lewis, Mount Prospect, both of IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/597,337

(22) Filed: Jun. 19, 2000

Related U.S. Application Data

(63) Continuation-in-part of application No. 09/281,118, filed on Mar. 29, 1999, now Pat. No. 6,099,737.

(51) Int. Cl.$^7$ .................................................. B10D 15/04
(52) U.S. Cl. ........................ 210/638; 210/646; 210/681; 210/903
(58) Field of Search ...................... 210/638, 645, 210/646, 681, 687, 691, 903, 905, 908, 909

(56) References Cited

U.S. PATENT DOCUMENTS

| | | | |
|---|---|---|---|
| 3,888,250 | 6/1975 | Hill | 128/214 R |
| 4,118,314 | 10/1978 | Yoshida | 210/22 C |
| 4,261,828 | 4/1981 | Brunner et al. | 210/287 |
| 4,581,141 | 4/1986 | Ash | 210/502 |
| 5,536,512 | 7/1996 | Ash | 210/645 |
| 6,099,737 | * 8/2000 | Sherman et al. | 210/691 |

FOREIGN PATENT DOCUMENTS 0 046 971  3/1982  (EP) .

* cited by examiner

*Primary Examiner*—Ivars Cintins
(74) *Attorney, Agent, or Firm*—John G. Tolomei; Frank S. Molinaro

(57) ABSTRACT

A process for removing toxins from fluids, such as bodily fluids or a dialysate solution, is disclosed. The process involves contacting the fluid with a microporous ion exchanger to remove toxins in the fluid. The microporous ion exchangers are represented by the following empirical formulae:

$$A_pM_xZr_{1-x}Si_nGe_yO_m \quad (I)$$

and $$A_pM_xTi_{1-x}Si_nGe_yO_m \quad (II)$$

24 Claims, No Drawings

PROCESS FOR REMOVING TOXINS FROM BODILY FLUIDS USING ZIRCONIUM OR TITANIUM MICROPOROUS COMPOSITIONS

CROSS-REFERENCE TO RELATED APPLICATION

This application is a Continuation-In-Part of application Ser. No. 09/281,118 filed Mar. 29, 1999, now U.S. Pat. No. 6,099,737, the contents of which are hereby incorporated by reference.

FIELD OF THE INVENTION

This invention relates to a process for removing toxins from fluids such as bodily fluids or dialysate solution. The fluid is contacted with a microporous ion exchange composition to remove toxins such as ammonium ions.

BACKGROUND OF THE INVENTION

In mammals, e.g., humans, when the kidneys and/or liver fail to remove metabolic waste products from the body, most of the other organs of the body also soon fail. Accordingly, extensive efforts have been made to discover safe and effective methods for removing toxins from patients' blood by extracorporeal treatment of the blood. Many methods have been proposed for removing small molecular toxins, protein-bound molecules or larger molecules thought to be responsible for the coma and illness of hepatic failure. Some of these toxic compounds have been identified as urea, creatine, ammonia, phenols, mercaptans, short chain fatty acids, aromatic amino acids, false neural transmitters (octopamine), neural inhibitors (glutamate) and bile salts. Among these, phenols and mercaptans, along with bilirubin and bacterial endotoxins, also occur as strong protein-bound toxins and are thus more difficult to effectively remove from the blood. Middle molecular weight toxins having a molecular weight of about 300 to about 10,000 can also be present and are difficult to effectively remove.

The art shows a number of ways to treat blood containing such toxins. The classic method is of course dialysis. Dialysis is defined as the removal of substances from a liquid by diffusion across a semipermeable membrane into a second liquid. Dialysis of blood outside of the body (hemodialysis) is the basis of the "artificial kidney." The artificial kidney treatment procedure generally used today is similar to that developed by Kolff in the early 1940s.

Since the 1940s there have been a number of disclosures which deal with improvements on artificial kidneys or artificial livers. Thus, U.S. Pat. No. 4,261,828 discloses an apparatus for the detoxification of blood. The apparatus comprises a housing filled with an adsorbent such as charcoal or a resin and optionally an enzyme carrier. In order to prevent direct contact between the blood and the adsorbent, the adsorbent may be coated with a coating which is permeable for the substances to be adsorbed yet prevent the direct contact between the corpuscular blood components and the adsorbents. U.S. Pat. No. 4,581,141 discloses a composition for use in dialysis which contains a surface adsorptive substance, water, a suspending agent, urease, a calcium-loaded cation exchanger, an aliphatic carboxylic acid resin and a metabolizable organic acid buffer. The calcium loaded cation exchanger can be a calcium-exchanged zeolite. EP 0 046 971 A1 discloses that zeolite W can be used in hemodialysis to remove ammonia. Finally, U.S. Pat. No. 5,536,412 discloses hemofiltration and plasmafiltration devices in which blood flows through the interior of a hollow fiber membrane and during the flow of blood, a sorbent suspension is circulated against the exterior surfaces of the hollow fiber membrane. Another step involves having the plasma fraction of the blood alternately exit and re-enter the interior of the membrane thereby effectuating removal of toxins. The sorbent can be activated charcoal along with an ion-exchanger such as a zeolite or a cation-exchange resin.

There are problems associated with the adsorbents disclosed in the above patents. For example, charcoal does not remove any water, phosphate, sodium or other ions. Zeolites have the disadvantage that they can partially dissolve in the dialysis solution, allowing aluminum and/or silicon to enter the blood. Additionally, zeolites can adsorb sodium, calcium and potassium ions from the blood thereby requiring that these ions be added back into the blood.

Applicants have developed a process which uses microporous ion exchangers which are essentially insoluble in fluids, such as bodily fluids (especially blood) or dialysis solutions. These microporous ion exchangers have an empirical formula on an anhydrous basis of:

$$A_p M_x Zr_{1-x} Si_n Ge_y O_m \quad (I)$$

or $$A_p M_x Ti_{1-x} Si_n Ge_y O_m \quad (II)$$

where A is an exchangeable cation selected from the group consisting of potassium ion, sodium ion, rubidium ion, cesium ion, calcium ion, magnesium ion, hydronium ion or mixtures thereof, M is at least one framework metal selected from the group consisting of hafnium (4+), tin (4+), niobium (5+), titanium (4+), cerium (4+), germanium (4+), praseodymium (4+), and terbium (4+), except that M is not titanium in formula (II), "p" has a value from about 1 to about 20, "x" has a value from zero to less than 1, "n" has a value from about 0 to about 12, "y" has a value from 0 to about 12, "m" has a value from about 3 to about 36 and $1 \leq n+y \leq 12$. The germanium can substitute for the silicon, zirconium/titanium or combinations thereof. Since these compositions are essentially insoluble in bodily fluids (at neutral or basic pH), they can be orally ingested in order to remove toxins in the gastrointestinal system.

SUMMARY OF THE INVENTION

As stated, this invention relates to a process for removing toxins from fluids selected from the group consisting of a bodily fluid, a dialysate solution and mixtures thereof, the process comprising contacting the fluid containing the toxins with a microporous ion exchanger at ion exchange conditions thereby removing the toxins from the fluid, the microporous ion exchanger selected from the group consisting of zirconium metallate, titanium metallate and mixtures thereof, the metallates respectively having an empirical formula on an anhydrous basis of:

$$A_p M_x Zr_{1-x} Si_n Ge_y O_m \quad (I)$$

and $$A_p M_x Ti_{1-x} Si_n Ge_y O_m \quad (II)$$

where A is an exchangeable cation selected from the group consisting of potassium ion, sodium ion, calcium ion, magnesium ion and mixtures thereof, M is at least one framework metal selected from the group consisting of hafnium (4+), tin (4+), niobium (5+), titanium (4+), cerium (4+), germanium (4+), praseodymium (4+), and terbium (4+), except that M is not titanium in formula (II), "p" has a value from about 1 to about 20, "x" has a value from zero to less than 1, "n" has a value from about 0 to about 12, "y" has a value from 0 to about 12, "m" has a value from about 3 to about 36 and $1 \leq n+y \leq 12$.

In a specific embodiment toxins are removed from the human body by:
  a) Filling the peritoneal cavity with a sufficient volume of dialysate solution such that the solution contacts the peritoneum for a sufficient time to remove toxins from the blood;
  b) Discharging the dialysate solution from the peritoneal cavity and flowing the dialysate solution through at least one bed containing the microporous ion exchanger described above at ion exchange conditions, thereby adsorbing the toxins on the exchanger; and
  c) Collecting a purified dialysate solution.

This and other objects and embodiments will become more clear after a detailed description of the invention.

DETAILED DESCRIPTION OF THE INVENTION

As stated, applicants have developed a new process for removing various toxins from fluids selected from bodily fluids and dialysate solution. One essential element of the instant process is a microporous ion exchanger which has a large capacity and strong affinity, i.e., selectivity for at least ammonia. These microporous compositions are identified as zirconium metallate and titanium metallate compositions. They are further identified by their empirical formulas (on an anhydrous basis) which respectively are:

$$A_p M_x Zr_{1-x} Si_n Ge_y O_m \qquad (I)$$

or $$A_p M_x Ti_{1-x} Si_n Ge_y O_m \qquad (II)$$

In the case of formula I, the composition has a microporous framework structure composed of $ZrO_3$ octahedral units and at least one of $SiO_2$ tetrahedral units and $GeO_2$ tetrahedral units. In the case of formula II, the microporous framework structure is composed of $TiO_3$ octahedral units and at least one of $SiO_2$ tetrahedral units and $GeO_2$ tetrahedral units.

In both formulas I and II, A is an exchangeable cation selected from the group consisting of potassium ion, sodium ion, rubidium ion, cesium ion, calcium ion, magnesium ion, hydronium ion or mixtures thereof, M is at least one framework metal selected from the group consisting of hafnium (4+), tin (4+), niobium (5+), titanium (4+), cerium (4+), germanium (4+), praseodymium (4+), and terbium (4+), "p" has a value from about 1 to about 20, "x" has a value from zero to less than 1, "n" has a value from about 0 to about 12, "y" has a value from 0 to about 12, "m" has a value from about 3 to about 36 and the sum of n+y has a value from about 1 to about 12. That is $1 \leq n+y \leq 12$. In equation (II) M is, of course, not titanium. The M metals which can be inserted into the framework in place of zirconium will be present as $MO_3$ octahedral units and thus it is a requirement that they are capable of being octahedrally coordinated. The germanium can be inserted into the framework in place of silicon and will be present as $MO_2$ tetrahedral units. Additionally, germanium can be inserted into the framework as a $MO_3$ octahedral unit replacing some of the zirconium in formula (I) or some of the titanium in formula (II). That is, germanium can replace some or all of the silicon, some of the zirconium in formula (I), some of the titanium in formula (II) or both silicon and zirconium or both silicon and titanium.

The zirconium metallates are prepared by a hydrothermal crystallization of a reaction mixture prepared by combining a reactive source of zirconium, silicon and/or germanium, optionally one or more M metal, at least one alkali metal and water. The alkali metal acts as a templating agent. Any zirconium compound, which can be hydrolyzed to zirconium oxide or zirconium hydroxide, can be used. Specific examples of these compounds include zirconium alkoxide, e.g., zirconium n-propoxide, zirconium hydroxide, zirconium acetate, zirconium oxychloride, zirconium chloride, zirconium phosphate and zirconium oxynitrate. The sources of silica include colloidal silica, fumed silica and sodium silicate. The sources of germanium include germanium oxide, germanium alkoxides and germanium tetrachloride. Alkali sources include potassium hydroxide, sodium hydroxide, rubidium hydroxide, cesium hydroxide, sodium carbonate, potassium carbonate, rubidium carbonate, cesium carbonate, sodium halide, potassium halide, rubidium halide, cesium halide, sodium ethylenediamine tetraacetic acid (EDTA), potassium EDTA, rubidium EDTA, and cesium EDTA. The M metals sources include the M metal oxides, alkoxides, halide salts, acetate salts, nitrate salts and sulfate salts. Specific examples of the M metal sources include, but are not limited to titanium alkoxides, titanium tetrachloride, titanium trichloride, titanium dioxide, tin tetrachloride, tin isopropoxide, niobium isopropoxide, hydrous niobium oxide, hafnium isopropoxide, hafnium chloride, hafnium oxychloride, cerium chloride, cerium oxide and cerium sulfate.

The titanium metallates are prepared in an analogous manner to the zirconium metallates. Thus, the sources of silicon, germanium, M metal and alkali metal are as enumerated above. The titanium source is also as enumerated above, namely titanium alkoxides, titanium tetrachloride, titanium trichloride and titanium dioxide. A preferred titanium source is titanium alkoxides with specific examples being titanium isopropoxide, titanium ethoxide and titanium butoxide.

Generally, the hydrothermal process used to prepare the zirconium metallate or titanium metallate ion exchange compositions of this invention involves forming a reaction mixture which in terms of molar ratios of the oxides is expressed by the formulae:

$$aA_2O:bMO_{q/2}:1-bZrO_2:cSiO_2:dGeO_2:eH_2O \qquad (III)$$

and $$aA_2O:bMO_{q/2}:1-bTiO_2:cSiO_2:dGeO_2:eH_2O \qquad (IV)$$

where "a" has a value from about 0.25 to about 40, "b" has a value from about 0 to about 1, "q" is the valence of M, "c" has a value from about 0.5 to about 30, "d" has a value from about 0 to about 30 and "e" has a value of 10 to about 3000. The reaction mixture is prepared by mixing the desired sources of zirconium, silicon and optionally germanium, alkali metal and optional M metal in any order to give the desired mixture. It is also necessary that the mixture have a basic pH and preferably a pH of at least 8. The basicity of the mixture is controlled by adding excess alkali hydroxide and/or basic compounds of the other constituents of the mixture. Having formed the reaction mixture it is next reacted at a temperature of about 100° C. to about 250° C. for a period of about 1 to about 30 days in a sealed reaction vessel under autogenous pressure. After the allotted time, the mixture is filtered to isolate the solid product which is washed with deionized water and dried in air.

As stated the microporous compositions of this invention have a framework structure of octahedral $ZrO_3$ units, at least one of tetrahedral $SiO_2$ units and tetrahedral $GeO_2$ units and optionally octahedral $MO_3$ units. This framework results in a microporous structure having an intracrystalline pore system with uniform pore diameters, i.e., the pore sizes are crystallographically regular. The diameter of the pores can vary considerably from about 3 Å and larger.

As synthesized, the microporous compositions of this invention will contain some of the alkali metal templating agent in the pores. These metals are described as exchangeable cations, meaning that they can be exchanged with other (secondary) A' cations. Generally, the A exchangeable cations can be exchanged with A' cations selected from other alkali metal cations ($K^+$, $Na^+$, $Rb^+$, $Cs^+$), alkaline earth cations ($Mg^{2+}$, $Ca^{2+}$, $Sr^{2+}$, $Ba^{2+}$), hydronium ion or mixtures thereof. It is understood that the A' cation is different from the A cation. The methods used to exchange one cation for another are well known in the art and involve contacting the microporous compositions with a solution containing the desired cation (at molar excess) at exchange conditions. Exchange conditions include a temperature of about 25° C. to about 100° C. and a time of about 20 minutes to about 2 hours. The particular cation (or mixture thereof which is present in the final product will depend on the particular use and the specific composition being used. One specific composition is an ion exchanger where the A' cation is a mixture of $Na^+$, $Ca^{+2}$ and $H^+$ ions.

It is also within the scope of the invention that these microporous ion exchange compositions can be used in powder form or can be formed into various shapes by means well known in the art. Examples of these various shapes include pills, extrudates, spheres, pellets and irregularly shaped particles.

As stated, these compositions have particular utility in adsorbing various toxins from fluids selected from bodily fluids, dialysate solutions, and mixtures thereof. As used herein and in the claims, bodily fluids will include but not be limited to blood and gastrointestinal fluids. Also by bodily is meant any mammalian body including but not limited to humans, cows, pigs, sheep, monkeys, gorillas, horses, dogs, etc. The instant process is particularly suited for removing toxins from a human body.

There are a number of means for directly or indirectly contacting the fluids with the desired ion exchanger and thus, remove the toxins. One technique is hemoperfusion, which involves packing the above described microporous ion exchange composition into a column through which blood is flowed. One such system is described in U.S. Pat. No. 4,261,828 which is incorporated by reference. As stated in the '828 patent, the microporous ion exchange composition is preferably formed into desired shapes such as spheres. Additionally, the microporous ion exchange composition particles can be coated with compounds, such as cellulose derivatives, which are compatible with the blood but nonpermeable for corpuscular blood components. In one specific case, spheres of the desired ion exchange compositions described above can be packed into hollow fibers thereby providing a semipermeable membrane. It should also be pointed out that more than one type of molecular sieve can be mixed and used in the process in order to enhance the efficiency of the process.

Another way of carrying out the process is to prepare a suspension or slurry of the molecular sieve adsorbent by means known in the art such as described is U.S. Pat. No. 5,536,412 which is incorporated by reference. The apparatus described in the '412 patent can also be used to carry out the process. The process basically involves passing a fluid, e.g. blood, containing toxins through the interior of a hollow fiber and during said passing circulating a sorbent suspension against the exterior surfaces of the hollow fiber membrane. At the same time, intermittent pulses of positive pressure are applied to the sorbent solution so that the fluid alternately exits and re-enters the interior of the hollow fiber membrane thereby removing toxins from the fluid.

The instant microporous ion exchange compositions can also be used in a conventional dialysis process where the blood is first contacted with a dialysis solution (dialysate) to remove uremic substances from the blood. The dialysate is now regenerated and recirculated. Regeneration is carried out by contacting the urea containing dialysate with urease to convert the urea to ammonium ion and carbonate ion according to the equation:

$$2H_2O + H_4N_2CO \rightarrow 2NH_4^+ + CO_3^-$$

In order for this reaction to proceed to completion, ammonium ions and carbonate ions must be removed. In the instant process, the microporous ion exchangers have a large capacity and selectivity for removing ammonium ions from the dialysate fluid. The urease can of course be immobilized on the microporous ion exchange compositions of the present invention. Details regarding bonding of urease to microporous compositions can be found in U.S. Pat. No. 4,581,141 which is incorporated by reference.

Another extracorporeal process uses a dialysate regeneration system called a REDY cartridge. The cartridge contains a system of sorbents including activated carbon, zirconium phosphate and hydrous zirconium oxide. The ammonium ions which are formed per the process described above using urease are absorbed by the zirconium phosphate in exchange for hydrogen and sodium ions. A description of the REDY cartridge may be found in a paper by A. Gordon and M. Roberts, published in *Sorbents and Their Clinical Applications*, C. Giordano editor, Academic Press, pp. 249–273 (1980) and especially p. 263–4 all of which are incorporated by reference.

Another type of dialysis is peritoneal dialysis. In peritoneal dialysis, the peritoneal cavity or the abdominal cavity (abdomen) is filled via a catheter inserted into the peritoneal cavity with a dialysate fluid or solution which contacts the peritoneum. Toxins and excess water flow from the blood through the peritoneum, which is a membrane that surrounds the outside of the organs in the abdomen, into the dialysate fluid. The dialysate remains in the body for a time (dwell time) sufficient to remove the toxins. After the required dwell time, the dialysate is removed from the peritoneal cavity through the catheter. There are two types of peritoneal dialysis. In continuous ambulatory peritoneal dialysis (CAPD), dialysis is carried out throughout the day. The process involves maintaining the dialysate solution in the peritoneal cavity and periodically removing the spent dialysate (containing toxins) and refilling the cavity with a fresh dialysate solution. This is carried out several times during the day. The second type is automated peritoneal dialysis or APD. In APD, a dialysate solution is exchanged by a device at night while the patient sleeps. In both types of dialyses, a fresh dialysate solution must be used for each exchange.

The zirconium and titanium metallates of the present invention can be used to regenerate the dialysate solutions used in peritoneal dialysis, thereby further decreasing the amount of dialysate that is needed to cleanse the blood and/or the amount of time needed to carry out the exchange. This regeneration is carried out by any of the means described above for conventional dialysis. For example, in an indirect contacting process, the dialysate from the peritoneal cavity, i.e. first dialysate is contacted with urease and the ammonium ions transferred across a membrane, thereby purifying the first dialysate solution, i.e. a purified dialysate solution. The second dialysate solution is flowed through at least one adsorption bed containing at least one microporous ion exchanger described above, thereby removing the ammonia and yielding a purified second dialysate solution. It is usually preferred to continuously circulate the second dialysate solution through the adsorbent bed until all of the ammonium ions have been removed. It is also preferred that the first dialysate solution be circulated through the peritoneal cavity, thereby increasing the ammonia removal efficiency and decreasing the total dwell time.

A direct contacting process can also be carried out in which the first dialysate solution is introduced into the peritoneal cavity and then flowed through at least one bed containing at least one microporous ion exchanger. As described above, this can be carried out as CAPD or APD.

The composition of the dialysate solution can be varied in order to ensure a proper electrolyte balance in the body. This is well known in the art along with various apparatus for carrying out the dialysis.

The zirconium metallates and titanium metallates can also be formed into pills or other shapes which can be ingested orally and pickup toxins in the gastrointestinal fluid as the ion exchanger passes through the intestines and is finally excreted. In order to protect the ion exchangers from the high acid content in the stomach, the shaped articles may be coated with various coatings which will not dissolve in the stomach, but dissolve in the intestines.

As has also been stated, although the instant compositions are synthesized with a variety of exchangeable cations ("A"), it is preferred to exchange the cation with secondary cations (A') which are more compatible with blood or do not adversely affect the blood. For this reason, preferred cations are sodium, calcium, hydronium and magnesium. Preferred compositions are those containing sodium and calcium or sodium, calcium and hydronium ions. The relative amount of sodium and calcium can vary considerably and depends on the microporous composition and the concentration of these ions in the blood.

In order to more fully illustrate the invention, the following examples are set forth. It is to be understood that the examples are only by way of illustration and are not intended as an undue limitation on the broad scope of the invention as set forth in the appended claims.

EXAMPLE 1

A solution was prepared by mixing 2058 g of colloidal silica (DuPont Corp. identified as Ludox® AS-40), 2210 g of KOH in 7655 g H2O. After several minutes of vigorous stirring 1471 g of a zirconium acetate solution (22.1 wt. % $ZrO_2$) were added. This mixture was stirred for an additional 3 minutes and the resulting gel was transferred to a stainless steel reactor and hydrothermally reacted for 36 hours at 200° C. The reactor was cooled to room temperature and the mixture was vacuum filtered to isolate solids which were washed with deionized water and dried in air.

The solid reaction product was analyzed and found to contain 21.2 wt. % Si, 21.5 wt. % Zr, K 20.9 wt. % K, LOI 12.8 wt. %, which gave a formula of $K_{2.3}ZrSi_{3.2}O_{9.5}*3.7H_2O$. This product was identified as sample A.

EXAMPLE 2

A solution was prepared by mixing 121.5 g of colloidal silica (DuPont Corp. identified as Ludox® AS-40), 83.7 g of NaOH in 1051 g H2O. After several minutes of vigorous stirring 66.9 g zirconium acetate solution (22.1 wt. % $ZrO_2$) was added. This was stirred for an additional 3 minutes and the resulting gel was transferred to a stainless steel reactor and hydrothermally reacted with stirring for 72 hours at 200° C. The reactor was cooled to room temperature and the mixture was vacuum filtered to isolate solids which were washed with deionized water and dried in air.

The solid reaction product was analyzed and found to contain 22.7 wt. % Si, 24.8 wt. % Zr, 12.8 wt. % Na, LOI 13.7 wt. %, which gives a formula $Na_{2.0}ZrSi_{3.0}O_{9.0}*3.5H_2O$. This product was identified as sample B.

EXAMPLE 3

A solution (60.08 g) of colloidal silica (DuPont Corp. identified as Ludox® AS-40) was slowly added over a period of 15 minutes to a stirring solution of 64.52 g of KOH dissolved in 224 g deionized $H_2O$. This was followed by the addition of 45.61 g zirconium acetate (Aldrich 15–16 wt. % Zr, in dilute acetic acid). When this addition was complete, 4.75 g hydrous $Nb_2O_5$ (30 wt. % LOI) was added and stirred for an additional 5 minutes. The resulting gel was transferred to a stirred autoclave reactor and hydrothermally treated for 1 day at 200° C. After this time, the reactor was cooled to room temperature, the mixture was vacuum filtered, the solid washed with deionized water and dried in air.

The solid reaction product was analyzed and found to contain 20.3 wt. % Si, 15.6 wt. % Zr, 20.2 wt. % K, 6.60 wt. % Nb, LOI 9.32 wt. %, which give a formula of $K_{2.14}Zr_{0.71}Nb_{0.29}Si_3O_{9.2} \cdot 2.32$ $H_2O$. Scanning Electron (SEM) of a portion of the sample, including EDAX of a crystal, indicated the presence of niobium, zirconium, and silicon framework elements. This product was identified as sample C.

EXAMPLE 4

$GeO_2$ (44.62 g) was slowly added to a stirring solution of 30.50 g of KOH dissolved in 140 g deionized $H_2O$. After the addition was complete, 45.82 g $ZrOCl_2 \cdot 8H_2O$ dissolved in 140 g deionized $H_2O$ was added drop-wise. The resulting gel was transferred to a stirred autoclave reactor and hydrothermally treated for 1 days at 200° C. After this time, the reactor was cooled to room temperature and the mixture was vacuum filtered, the solid was washed with deionized water and dried in air.

The solid reaction product was analyzed and found to contain 41.0 wt. % Ge, 18.4 wt. % Zr, 12.0 wt. % K, LOI 6.39 wt. %, which gave a formula of $K_{1.52}ZrGe_{2.80}O_{8.36} \cdot 1.84H_2O$. This product was identified as sample D.

EXAMPLE 5

Into a 2-liter beaker, 350.0 g of tetraethylorthosilicate (98%) and 160.83 g of titanium tetraisopropoxide (97%) were placed and stirred with a high speed mechanical mixer. Separately, 106.30 g KOH (87%) was dissolved in 768.5 g of deionized water. This solution was then added to the stirring alkoxides and agitated for an additional two hours. The reaction mixture was then transferred to a 2-liter stirred autoclave where it was digested at a temperature of 200° C. for 132 hr. while stirring at 100 rpm. The product was isolated by filtration, washed thoroughly with deionized water and dried at 100° C.

Elemental analysis of the product gave an empirical formula of $K_{1.95}Si_{2.94}TiO_{8.85}$. X-ray diffraction analysis showed that this product had the same topology as the mineral umbite. This product was identified as sample E.

EXAMPLE 6

Into a 2-liter beaker, there were mixed 380.0 g of tetraethylorthosilicate (98%) and 104.8 g of titanium tetraisopropoxide (97%). Separately, a sodium hydroxide solution was prepared by dissolving 58.90 g NaOH (97%) in 854.73 g deionized water This solution was added to the alkoxide mixture as it was stirred vigorously with a mechanical stirrer. The reaction mixture was stirred for 2 hours before it was introduced into a 2-liter autoclave. The reaction mixture was reacted at 200° C. at autogenous pressure for 132 hrs. The product was isolated by filtration, washed with deionized water, and dried at 100° C.

Elemental analysis showed that this product had the empirical formula $Na_{2.05}Si_{3.72}TiO_{10.47}$. X-ray diffraction analysis showed that this product had the same topology as the mineral zorite. This product was identified as sample F.

EXAMPLE 7

Samples A to F and zeolite W (obtained from UOP LLC) were tested for removal of ammonium ions using the following procedure. If the compositions were not synthesized in the sodium form (zeolite W was obtained in the potassium form), the compositions were converted to the predominantly sodium form by contacting the compositions with a solution containing a molar excess (at least 10 fold) of sodium chloride thereby exchanging the sodium for the potassium. The exchange conditions were those typical in the art. A test solution was prepared by mixing 6 mL of a dialysate concentrate with 194 mL of deionized water and 0.7 g of ammonium chloride ($NH_4Cl$). The final composition of this dialysate test solution is shown in Table 1.

TABLE 1

Dialysate Test Solution Composition

| Element | mEq/L |
|---|---|
| Na | 134 |
| Ca | 2.5 |
| K | 0 |
| Mg | 1.5 |
| $NH_4$ | 65 |

Into a 25 mL vial, there were added 100 mg of the sample to be tested, to which there were added 10 ml of the above test dialysis solution. The vial was placed in an upright shaker and agitated at 37° C. for about 10–18 hours. The mixture was then filtered and the filtrate analyzed for $NH_4^+$ concentration by ion chromatography. Based on this analysis, the particular sample's ability to ion exchange ammonium ions was determined by calculating the ammonium ($NH_4^+$) distribution coefficient ($K_d$) by using the following formula:

$$K_d(mL/g) = \frac{(V)(Ac)}{(W)(Sc)}$$

where: V=volume of test dialysate (mL)
Ac=concentration of cation absorbed on ion-exchanger (g/mL)

W=mass of ion-exchanger evaluated (g)
Sc=concentration of cation in post reaction supernate (g/mL)

The results of the testing are presented in Table 2.

TABLE 2

Ammonium $K_d$ for several molecular sieves

| Sample I.D. | $K_d$ |
|---|---|
| A | 178 |
| B | 79 |
| C | 100 |
| D | 58 |
| E | 17 |
| F | 10 |
| Zeolite W | 90 |

The results in Table 2 show that the compositions of the present invention have a wide range of $K_d$ for ammonium ion and are suitable for removing toxins from blood.

EXAMPLE 8

To a solution prepared by mixing 141.9 g of NaOH pellets in 774.5 g of water, there were added 303.8 g of sodium silicate with stirring. To this mixture there were added dropwise, 179.9 g of zirconium acetate (15% Zr in a 10% acetic acid solution). After thorough blending, the mixture was transferred to a Hastalloy™ reactor and heated to 200° C. under autogenous pressure with stirring for 72 hours. At the end of the reaction time, the mixture was cooled to room temperature, filtered and the solid product was washed with a 0.001 M NaOH solution and then dried at 100° C. for 16 hours. Analysis by x-ray powder diffraction showed that the product was pure UZSi-11.

EXAMPLE 9

To a container there was added a solution of 37.6 g NaOH pellets dissolved in 848.5 g water and to this solution there were added 322.8 g of sodium silicate with mixing. To this mixture there were added dropwise 191.2 g of zirconium acetate (15% Zr in 10% acetic acid). After thorough blending, the mixture was transferred to a Hastalloy™ reactor and the reactor was heated to 200° C. under autogenous conditions with stirring for 72 hours. Upon cooling, the product was filtered, washed with 0.001 M NaOH solution and then dried at 100° C. for 16 hours. X-ray powder diffraction analysis showed the product to be UZSi-9.

EXAMPLE 10

Samples of UZSi-11, UZSi-9 and Zr phosphate taken from a REDY cartridge were tested for ammonia adsorption using a similar test to that described in Example 7. A dialysate solution containing the following ions was used for the test: 0.096 wt. % $NH_4^+$; 0.29 wt. % $Na^+$; 0.003 wt. % $K^+$; 0.0017 wt. % Mg and 0.0048 wt. % Ca. To a vial there were added 0.02 g of the sample and 10 ml of dialysate solution. The vial was placed in an upright shaker and agitated for 1440 minutes. The mixture was then filtered and the filtrate analyzed for $NH_4^+$ concentration by ion chromatography. $K_d$ values were calculated as in example 7. The results for these samples are presented in Table 3.

TABLE 3

Ammonium K$_d$ for Different Adsorbents

| Sample I.D. | K$_d$ |
|---|---|
| UZSi-9 | 490 |
| UZSi-11 | 76 |
| Zr Phosphate | 50 |

We claim as our invention:

1. A process for removing toxins from a fluid selected from the group consisting of a bodily fluid and a dialysate solution, the process comprising contacting the fluid containing the toxins with a microporous ion exchanger at ion exchange conditions thereby removing the toxins from the fluid, the microporous ion exchanger selected from the group consisting of zirconium metallate, titanium metallate and mixtures thereof, the metallates respectively having an empirical formula on an anhydrous basis of:

$$A_pM_xZr_{1-x}Si_nGe_yO_m \quad (I)$$

and $$A_pM_xTi_{1-x}Si_nGe_yO_m \quad (II)$$

where A is an exchangeable cation selected from the group consisting of potassium ion, sodium ion, calcium ion, magnesium ion and mixtures thereof, M is at least one framework metal selected from the group consisting of hafnium (4+), tin (4+), niobium (5+), titanium (4+), cerium (4+), germanium (4+), praseodymium (4+), and terbium (4+), except that M is not titanium in formula (II), "p" has a value from about 1 to about 20, "x" has a value from zero to less than 1, "n" has a value from about 0 to about 12, "y" has a value from 0 to about 12, "m" has a value from about 3 to about 36 and $1 \leq n+y \leq 12$.

2. The process of claim 1 where the fluid is a bodily fluid selected from the group consisting of blood and gastrointestinal fluid.

3. The process of claim 2 where the microporous ion exchanger is orally ingested and contacted with gastrointestinal fluids of the body thereby removing toxins from said fluids.

4. The process of claim 1 where the fluid is a dialysate solution.

5. The process of claim 4 further comprising flowing the dialysate solution through a bed containing the microporous ion exchanger for a time sufficient to remove toxins from the dialysate solution.

6. The process of claim 1 where the toxin is ammonium ions.

7. The process of claim 1 where M is tin (+4).

8. The process of claim 1 where M is titanium (+4).

9. The process of claim 1 where M is niobium (5+).

10. The process of claim 1 where n=0.

11. The process of claim 1 where the A cation is exchanged for a different secondary cation, A', selected from the group consisting of alkali metals, alkaline earth metal, hydronium ions and mixtures thereof.

12. The process of claim 11 where A' is a mixture of sodium and calcium ions.

13. The process of claim 11 where A' is a mixture of sodium, calcium and hydronium ions.

14. A process for removing toxins from a mammalian body comprising:

a) filling the peritoneal cavity with a sufficient volume of a first dialysate solution such that the solution contacts the peritoneum for a sufficient time to remove toxins from the blood;

b) discharging the first dialysate solution from the peritoneal cavity and contacting the first dialysate solution with a microporous ion exchanger at ion exchange conditions, thereby adsorbing the toxins onto the ion exchanger; and c) collecting a purified dialysate solution;

the microporous ion exchanger selected from the group consisting of zirconium metallate, titanium metallate and mixtures thereof, the metallates respectively having an empirical formula on an anhydrous basis of:

$$A_pM_xZr_{1-x}Si_nGe_yO_m \quad (I)$$

and $$A_pM_xTi_{1-x}Si_nGe_yO_m \quad (II)$$

where A is an exchangeable cation selected from the group consisting of potassium ion, sodium ion, calcium ion, magnesium ion and mixtures thereof, M is at least one framework metal selected from the group consisting of hafnium (4+), tin (4+), niobium (5+), titanium (4+), cerium (4+), germanium (4+), praseodymium (4+), and terbium (4+), except that M is not titanium in formula (II), "p" has a value from about 1 to about 20, "x" has a value from zero to less than 1, "n" has a value from about 0 to about 12, "y" has a value from 0 to about 12, "m" has a value from about 3 to about 36 and $1 \leq n+y \leq 12$.

15. The process of claim 14 where the contacting of step (b) is carried out by flowing the dialysate solution through at least one bed containing a microporous ion exchanger.

16. The process of claim 14 where the contacting of step (b) is carried out by contacting the first dialysate solution with a semipermeable membrane such that the toxins flow through the membrane into a second dialysate solution and flowing the second dialysate solution through at least one bed containing a microporous ion exchanger.

17. The process of claim 14 where the purified dialysate solution is continuously recirculated to step (a) and steps (a) to (c) are carried out continuously.

18. The process of claim 14 where M is tin (+4).

19. The process of claim 14 where M is titanium (4+).

20. The process of claim 14 where M is niobium (5+).

21. The process of claim 14 where n=0.

22. The process of claim 14 where the A cation is exchanged for a different secondary cation, A', selected from the group consisting of alkali metals, alkaline earth metal, hydronium ions and mixtures thereof.

23. The process of claim 22 where A' is a mixture of sodium and calcium ions.

24. The process of claim 22 where A' is a mixture of sodium, calcium and hydronium ions.

* * * * *